(12) United States Patent
Holschuh et al.

(10) Patent No.: US 6,548,253 B1
(45) Date of Patent: Apr. 15, 2003

(54) METHOD OF ISOLATING PLASMID DNA

(75) Inventors: Karl Holschuh, Seeheim-Jugenheim (DE); Uwe Michelsen, Weinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/830,956

(22) PCT Filed: Oct. 26, 1999

(86) PCT No.: PCT/EP99/08091

§ 371 (c)(1), (2), (4) Date: Jun. 8, 2001

(87) PCT Pub. No.: WO00/29562

PCT Pub. Date: May 25, 2000

(30) Foreign Application Priority Data

Nov. 6, 1998 (DE) .......................... 198 51 156

(51) Int. Cl.[7] .......................... C12Q 1/68; C07H 19/00; C07H 21/04
(52) U.S. Cl. .......................... 435/6; 536/22.1; 536/25.4
(58) Field of Search .............................. 435/6; 536/22.1, 536/25.4, 26.42

(56) References Cited

U.S. PATENT DOCUMENTS

| | | | |
|---|---|---|---|
| 5,051,189 A | 9/1991 | Farrah | 210/679 |
| 5,075,430 A | 12/1991 | Little | 536/27 |
| 5,378,621 A * | 1/1995 | Lawlis, Jr. et al. | 435/183 |
| 6,255,477 B1 * | 7/2001 | Kleiber et al. | 536/25.4 |

FOREIGN PATENT DOCUMENTS

| | | |
|---|---|---|
| DE | 4307262 | 9/1994 |
| DE | 19520398 | 12/1996 |
| WO | 9207863 | 5/1992 |

OTHER PUBLICATIONS

Carter MJ et al. An inexpensive and simple method for DNA purifications on silica particles. Nucleic Acids. Res., 21(4): 1044, 1993.*

* cited by examiner

Primary Examiner—Jeffrey Fredman
Assistant Examiner—Suryaprabha Chunduru
(74) Attorney, Agent, or Firm—Millen, White, Zelano & Branigan, P.C.

(57) ABSTRACT

The invention relates to a method of isolating plasmid DNA from microorganism cultures with the aid of solid-phase bodies. The solid-phase bodies can be silica gels, silicates, or glass-like materials and the solid-phase bodies can have magnetic properties. The solid-phase bodies are used for isolating the microorganisms and for isolating the plasmid DNA.

8 Claims, No Drawings

METHOD OF ISOLATING PLASMID DNA

The invention relates to a method of isolating plasmid DNA from microorganism cultures with the aid of solid-phase bodies.

In molecular biology, microorganisms (for example Escherichia coli, Salmonella typhimurium, etc.) have long been used for cloning experiments. To this end, extrachromasomal DNA, so-called plasmid DNA, is, employed as a vehicle for the specific DNA fragments to be cloned. It is an everyday task for the person skilled in the art to find the correct bacterial population with the desired plasmid clone. Various chemical methods for the isolation of plasmid DNA from microorganisms have been described. It is a common feature of all these methods that the microorganisms are firstly separated off by centrifugation in order to remove the nutrient medium. The nutrient medium must be removed as quantitatively as possible, and the microorganism precipitate obtained must be resuspended completely in a resuspension buffer.

The present invention has the object of providing a method of isolating plasmid DNA from microorganisms which does not require a centrifugation step for the removal of the nutrient medium.

The invention relates to a method of isolating plasmid DNA from microorganism cultures with the aid of solid-phase bodies which is characterised in that
a) the microorganism culture is brought to an acidic pH, mixed with the solid-phase bodies, incubated and separated off,
b) the microorganisms immobilized on the solid-phase bodies are resuspended, lysed, mixed with a neutralising binding buffer and incubated, and the solid-phase bodies are separated off and discarded,
c) the supernatant is again mixed with solid-phase bodies, incubated and subsequently separated off, and the plasmid DNA is eluted from the solid-phase bodies using an elution buffer.

Suitable solid-phase bodies are silica gels, silicates or glass-like materials, preferably magnetic solid-phase bodies having a silica-gel surface, in particular magnetic silica particles.

Surprisingly, it has been found that, under certain buffer conditions, bacteria bind non-specifically to magnetisable solid-phase bodies having a silica-gel surface and can be separated off magnetically directly from the nutrient medium. It has furthermore been found that the bacteria collected in this way can be resuspended, lysed and likewise separated off as a compact magnetic precipitate together with the genomic DNA, leaving the plasmid DNA in the supernatant. The invention is distinguished by the fact that it makes all method steps of the plasma isolation automatable.

The method according to the invention is carried out, for example, by adjusting a bacterial culture which has been incubated overnight in a growth medium to an acidic pH with the aid of buffers or acids. Magnetic particles are subsequently added, the mixture is incubated for a few minutes, and the particles are separated off in a magnetic field. The supernatant is discarded, and the bacteria adhering to the particles are resuspended in a resuspension buffer. A lysis buffer is then added, mixed and incubated for a few minutes at room temperature; a neutralising binding buffer (N-binding buffer) is added and mixed, and the particles are separated off in a magnetic field. The supernatant is transferred into a fresh reagent vessel, particles are added, mixed and separated off in a magnetic field. The particles with the bound plasmid DNA are washed with washing buffer, and finally the plasmid DNA is eluted with elution buffer.

The microorganism cultures are preferably E. coli or E. coli mutants, such as W3110, JM109, RR1, XL-1 Blue, inter alia. These cultures are generally incubated overnight at 37° C., for example in an LB medium (10 g of Trypton, 5 g of yeast extract, 10 g of common salt per litre).

A culture prepared in a corresponding manner is adjusted to a pH in the range from 1 to 4, preferably pH 2, with the aid of buffers or acids. Suitable buffers are those which have an adequate buffer capacity in this pH range, for example formate, acetate or citrate buffer, or also acids, such as hydrochloric acid. 1 ml of the bacterial culture is acidified, for example using 0.1 ml of 1N hydrochloric acid, and mixed with 5–50 $\mu$l of a suspension (50 mg/ml) of magnetic silica particles, incubated for 1 minute and separated off in a magnetic field. It has been found that 5–15 $\mu$l of the particle suspension are generally sufficient to separate off more than 50% of the bacteria. The number of particles used here exceeds the number of bacteria approximately by a factor of 10–30.

The bacteria adhering to the particles are resuspended in a resuspension buffer. The buffer should be capable of maintaining a pH in the range from 7 to 9; a suitable resuspension buffer consists, for example, of tris-HCl, EDTA and RNase A.

A lysis buffer is added to the resuspended bacteria, mixed and incubated at room temperature for a few minutes. The lysis buffer consists, for example, of sodium hydroxide solution and SDS. A neutralising binding buffer (N-binding buffer) is subsequently added and mixed, and the particles are separated off in a magnetic field and discarded. The N-binding buffer should maintain a pH in the range from 4 to 6; a suitable N-binding buffer consists, for example, of a guanidinium salt and potassium acetate. However, the two buffer components can also be employed separately and successively (see Example 2).

The supernatant is transferred into a fresh reagent vessel, further particles are added and mixed, and the particles loaded with the plasmid DNA are separated off in a magnetic field and washed with washing buffer. This buffer should buffer in the pH range from 5 to 7, with the DNA remaining bound to the particles. A suitable washing buffer consists, for example, of tris-HCl and EDTA.

Subsequent elution of the plasmid DNA is carried out using an elution buffer. The elution buffer used for this purpose should maintain a pH in the range from 7.5 to 9.5, preferably from 8 to 9. Examples of suitable buffers are tris-HCl buffer, tricine, bicine and other buffers which buffer in this pH range, preferably tris-HCl. If desired, the elution buffer may contain chelating agents, such as EDTA, and/or other substances. The buffer concentration should be from 5 to 10 mM, preferably about 10 mM. If desired, the buffer may also contain small amounts of EDTA, for example 1 mM. The nucleic acid eluted in this way can be employed directly, without further purification steps, for molecular-biological applications, such as, for example, for amplification reactions (PCR, NASBA).

Example 1

Materials

Microcentrifuge tubes
Particle suspension: 50 mg/ml
Resuspension buffer: 50 mM tris-HCl, pH 8.0/10 mM EDTA/5 mg/ml RNase A
Lysis buffer: 200 mM NaOH/1% SDS
N-binding buffer: 5.3 M Gua-HCl/0.7 M potassium acetate, pH 4.8
Washing buffer: 10 mM tris-HCl/1 mM EDTA, pH 6.5
Elution buffer: 10 mM tris-HCl/1 mM EDTA, pH 8.5

Method steps

1. A bacterial culture (1 ml) is mixed with 0.1 ml of 1 N hydrochloric acid and 10 $\mu$l of magnetic silica particles, incubated for 1 minute and separated off in a magnetic field, 2. the supernatant is discarded, and the bacteria adhering to the particles are resuspended in 100 μl of resuspension buffer,
3. 200 μl of lysis buffer are added, mixed and incubated for 5 minutes,
4. 400 μl of N-binding buffer are added and mixed, and the particles are separated off,
5. the supernatant is transferred into a fresh microcentrifuge tube,
6. 10 μl of particle suspension are added and mixed, and the particles are separated off; the supernatant is discarded,
7. the particles are washed twice with washing buffer and eluted with 50 μl of elution buffer.

Example 2

Materials

Microcentrifuge tubes
Particle suspension: 50 mg/ml
Resuspension buffer: 50 mM tris-HCl, pH 8.0/10 mM EDTA/5 mg/ml
RNase A
Lysis buffer: 200 mM NaOH/1% SDS
Neutralisation buffer: 3 M potassium acetate, pH 5.5
Binding buffer: 5 M guanidinium thiocyanate
Washing buffer: 10 mM tris-HCl/1 mM EDTA, pH 6.5
Elution buffer: 10 mM tris-HCl/1 mM EDTA, pH 8.5

Method steps

1. A bacterial culture (1 ml) is mixed with 50 μl of 1 N hydrochloric acid and 10 μl of magnetic silica particles, incubated for five minutes and separated off in a magnetic field,
2. the supernatant is discarded, and the bacteria adhering to the particles are resuspended in 200 μl of resuspension buffer,
3. 200 μl of lysis buffer are added, mixed and incubated for 5 minutes,
4. 200 μl of neutralisation buffer are added and mixed, and the particles are separated off together with the precipitate,
5. the supernatant is transferred into a fresh microcentrifuge tube,
6. the same volume of binding buffer and at least 10 μl of particle suspension are added and mixed, and the particles are separated off; the supernatant is discarded,
7. the particles are washed twice with washing buffer and the plasmid DNA is eluted with 50 μl of elution buffer.

What is claimed is:

1. A method of isolating plasmid DNA from a microorganism culture with the aid of solid-phase bodies, comprising:

a) acidifying said culture to an acid pH and mixing said culture with solid-phase bodies which are underivatized with antibody and which nonspecifically immobilize microorganisms thereon, b) resuspending the immobilized microorganisms, lysing the microorganisms, adding a neutralising binding buffer and incubating the buffer with the lysed microorganisms, followed by removing and discarding the solid-phase bodies, c) mixing the supernatant from step (b), containing plasmid DNA, with solid-phase bodies and incubating the supernatant with the bodies followed by eluting the plasmid DNA from the solid-phase bodies with an elution buffer.

2. The method according to claim 1, wherein the microorganism is an *Escherichia coli* or an *Escherichia colt* mutant.

3. The method according to claim 1, wherein the solid-phase bodies are magnetic solid-phase bodies having a silica gel surface.

4. The method according to claim 3, wherein the magnetic solid-phase bodies are silica gels, silicates, or a glass-like materials.

5. The method according to claim 3, wherein the magnetic-solid phase bodies are silica particles.

6. The method according to claim 1, wherein the acid pH is in the range from about pH 1 to about pH 4 using the aid of buffers or acids.

7. The method according to claim 6, wherein the pH is set using hydrochloric acid.

8. A method of isolating plasmid DNA from a microorganism culture with the aid of magnetic solid-phase bodies having a solid gel surface, comprising:

a) acidifying said culture to an acid pH and mixing said culture with magnetic solid-phase bodies having a solid gel surface which nonspecifically immobilize microoganisms thereon, b) resuspending the immobilized microorganisms, lysing the microorganisms, adding a neutralising binding buffer and incubating the buffer with the lysed microorganisms, followed by removing and discarding the magnetic solid-phase bodies having a solid gel surface, c) mixing the supernatant from step (b), containing plasmid DNA, with magnetic solid-phase bodies having a solid gel surface and incubating the supernatant with the bodies followed by eluting the plasmid DNA from the magnetic solid-phase bodies having a solid gel surface with an elution buffer.

* * * * *